United States Patent
Howell

(10) Patent No.: US 12,279,910 B2
(45) Date of Patent: Apr. 22, 2025

(54) ULTRASOUND IMAGING SYSTEM WITH A STERILIZING SYSTEM

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 121 days.

(21) Appl. No.: 18/125,029

(22) Filed: Mar. 22, 2023

(65) Prior Publication Data

US 2023/0301626 A1 Sep. 28, 2023

Related U.S. Application Data

(60) Provisional application No. 63/322,540, filed on Mar. 22, 2022.

(51) Int. Cl.
*A61B 8/00* (2006.01)
*A61L 2/10* (2006.01)
(Continued)

(52) U.S. Cl.
CPC .......... *A61B 8/4444* (2013.01); *A61B 8/4254* (2013.01); *A61B 8/4422* (2013.01);
(Continued)

(58) Field of Classification Search
CPC ................ A61B 8/4422; A61N 5/0624; A61N 2005/0661; A61N 2005/0644
See application file for complete search history.

(56) References Cited

U.S. PATENT DOCUMENTS

| 6,908,460 B2 | 6/2005 | DiStefano |
| 8,372,128 B2 | 2/2013 | Reuben |

(Continued)

FOREIGN PATENT DOCUMENTS

| CA | 2199384 C | 6/2006 |
| CN | 106308727 A | 1/2017 |

(Continued)

OTHER PUBLICATIONS

PCT/US2023/015961 filed Mar. 22, 2023, International Search Report and Written Opinion dated Jul. 17, 2023.

(Continued)

*Primary Examiner* — Colin T. Sakamoto
(74) *Attorney, Agent, or Firm* — Rutan & Tucker LLP

(57) ABSTRACT

An ultrasound imaging system configured to simultaneously capture one or more ultrasound images and sterilize a skin surface within a target area via ultraviolet light. The ultrasound imaging system includes an ultrasound probe having an ultrasound array configured to capture the one or more ultrasound images of a target area. A sterilizing system of the ultrasound probe includes a plurality of ultraviolet light sources. Logic of the ultrasound imaging system governs the operation of the ultraviolet light sources including activation, deactivation, intensity modulation, and/or pulsing modulation. Contact and motion sensors provide input to the logic and the logic governs operation of the ultraviolet light sources in accordance input received from the contact and motion sensors.

26 Claims, 8 Drawing Sheets

(51) Int. Cl.
  *A61L 2/26* (2006.01)
  *A61N 5/06* (2006.01)
(52) U.S. Cl.
  CPC ............... *A61B 8/54* (2013.01); *A61L 2/10* (2013.01); *A61L 2/26* (2013.01); *A61N 5/0624* (2013.01); *A61L 2202/11* (2013.01); *A61L 2202/24* (2013.01); *A61N 2005/0644* (2013.01); *A61N 2005/0661* (2013.01)

(56) References Cited

U.S. PATENT DOCUMENTS

| | | | |
|---|---|---|---|
| 8,387,405 | B2 | 3/2013 | Johnson |
| 9,592,374 | B2 | 3/2017 | Muse |
| 9,604,072 | B2 | 3/2017 | Brezinski |
| 9,981,052 | B2 | 5/2018 | Clynne et al. |
| 2008/0027399 | A1 | 1/2008 | Harding et al. |
| 2008/0283769 | A1 | 11/2008 | Deshays |
| 2011/0144566 | A1 | 6/2011 | Dacey, Jr. et al. |
| 2012/0116294 | A1 | 5/2012 | Boenig et al. |
| 2013/0303996 | A1 | 11/2013 | Rasooly et al. |
| 2013/0323119 | A1 | 12/2013 | Alwan |
| 2013/0323120 | A1 | 12/2013 | Ma |
| 2014/0257186 | A1 | 9/2014 | Kerr |
| 2015/0148734 | A1 | 5/2015 | Fewkes et al. |
| 2015/0157209 | A1 | 6/2015 | Dantus |
| 2015/0165185 | A1 | 6/2015 | Cohen et al. |
| 2015/0283277 | A1 | 10/2015 | Schafer et al. |
| 2016/0038621 | A1 | 2/2016 | Victor et al. |
| 2016/0151639 | A1 | 6/2016 | Scharf et al. |
| 2016/0310077 | A1 | 10/2016 | Hunter et al. |
| 2017/0136209 | A1 | 5/2017 | Burnett et al. |
| 2017/0196478 | A1 | 7/2017 | Hunter |
| 2017/0296142 | A1 | 10/2017 | Wodecki et al. |
| 2018/0369560 | A1 | 12/2018 | Ball et al. |
| 2019/0111240 | A1 | 4/2019 | Fia et al. |
| 2019/0151587 | A1 | 5/2019 | Vazales et al. |
| 2019/0192872 | A1 | 6/2019 | Schwarz et al. |
| 2019/0290791 | A1 | 9/2019 | Baker et al. |
| 2019/0374668 | A1 | 12/2019 | Kopperschmidt et al. |
| 2020/0030473 | A1 | 1/2020 | Sugimoto et al. |
| 2020/0147248 | A1 | 5/2020 | Mintie et al. |
| 2020/0188543 | A1 | 6/2020 | Etter et al. |
| 2020/0324078 | A1 | 10/2020 | Motley et al. |
| 2021/0113725 | A1 | 4/2021 | Etter et al. |
| 2021/0154342 | A1 | 5/2021 | Canfield |
| 2021/0204818 | A1 | 7/2021 | Akins et al. |
| 2021/0236859 | A1 | 8/2021 | Park et al. |
| 2022/0016439 | A1 | 1/2022 | Shah et al. |
| 2022/0347456 | A1 | 11/2022 | Messerly |
| 2022/0387643 | A1 | 12/2022 | Baarman |
| 2023/0118324 | A1* | 4/2023 | Hong ............... A61B 8/4483 73/632 |
| 2024/0115749 | A1 | 4/2024 | Payne et al. |
| 2024/0188859 | A1 | 6/2024 | Fellner et al. |
| 2024/0189467 | A1 | 6/2024 | Urry et al. |
| 2024/0226350 | A1 | 7/2024 | Payne et al. |
| 2024/0226351 | A1 | 7/2024 | Payne et al. |
| 2024/0226352 | A1 | 7/2024 | Fellner et al. |
| 2024/0252789 | A1 | 8/2024 | Hayden et al. |
| 2024/0335636 | A1 | 10/2024 | Laine et al. |
| 2024/0342325 | A1 | 10/2024 | Urry et al. |

FOREIGN PATENT DOCUMENTS

| | | |
|---|---|---|
| CN | 208481489 U | 2/2019 |
| CN | 209790441 U | 12/2019 |
| CN | 213373944 U | 6/2021 |
| CN | 213551294 U | 6/2021 |
| CN | 113101207 A | 7/2021 |
| CN | 213642120 U | 7/2021 |
| CN | 113476076 A | 10/2021 |
| CN | 215426269 U | 1/2022 |
| EP | 3195805 A1 | 7/2017 |
| JP | 2005198761 A | 7/2005 |
| KR | 20140003473 U | 6/2014 |
| KR | 101654328 B1 | 9/2016 |
| KR | 20220000634 U | 3/2022 |
| KR | 20220063891 A | 5/2022 |
| KR | 102452057 B1 | 10/2022 |
| WO | 2011068545 A1 | 6/2011 |
| WO | 2013134421 A1 | 9/2013 |
| WO | 2014165854 A1 | 10/2014 |
| WO | 2015157518 A1 | 10/2015 |
| WO | 2021146701 A1 | 7/2021 |
| WO | 2021157769 A1 | 8/2021 |
| WO | 2022036886 A1 | 2/2022 |
| WO | 2022046138 A1 | 3/2022 |
| WO | 2022200038 A2 | 9/2022 |
| WO | 2022232479 A1 | 11/2022 |
| WO | 2023183426 A1 | 9/2023 |
| WO | 2024081335 A1 | 4/2024 |
| WO | 2024124112 A1 | 6/2024 |
| WO | 2024129817 A1 | 6/2024 |
| WO | 2024151420 A1 | 7/2024 |
| WO | 2024151421 A1 | 7/2024 |
| WO | 2024151648 A1 | 7/2024 |
| WO | 2024163670 A1 | 8/2024 |

OTHER PUBLICATIONS

PCT/US2023/034981 filed Oct. 11, 2023, International Search Report and Written Opinion dated Dec. 11, 2023.
PCT/US2024/024136 filed Apr. 11, 2024, International Search Report and Written Opinion dated Sep. 18, 2024.
PCT/US2024/024969 filed Apr. 17, 2024, International Search Report and Written Opinion dated Sep. 27, 2024.
PCT/US2024/028630 filed May 9, 2024, International Search Report and Written Opinion dated Sep. 18, 2024.
Cabral, J. et al., "Blue Light Disinfection in Hospital Infection Control: Advantages, Drawbacks, and Pitfalls." Antibiotics, 2019.
Cabral, João, and Rodrigues A. G. "Blue light disinfection in hospital infection control: advantages, drawbacks, and pitfalls." Antibiotics 8.2 (2019): 58.
Changtong et al., "A porphyrin molecule that generates, traps, stores, and releases singlet oxygen.", Journal of Photochemistry and Photobiology A: Chemistry 260 (Sep. 13, 2013).
Changtong, Chuchawin, et al. "A porphyrin molecule that generates, traps, stores, and releases singlet oxygen." Journal of Photochemistry and Photobiology A: Chemistry 260 (2013): 9-13.
Halstead, F.D., Ahmed, Z., Bishop, J.R.B. et al. "The potential of visible blue light (405nm) as a novel decontamination strategy for carbapenemase-producing enterobacteriaceae (CPE)." Antimicrob Resist Infect Control 8, 14 (2019).
Halstead, Fenella D., et al. "The potential of visible blue light (405 nm) as a novel decontamination strategy for carbapenemase-producing enterobacteriaceae (CPE)." Antimicrobial Resistance & Infection Control 8.1 (2019): 1-8.
PCT/US2022/026888 filed Apr. 29, 2022 International Search Report and Writtent Opinion dated Jul. 29, 2022.
Tsen et al., "Inactivation of multidrug-resistant bacteria and bacterial spores and generation of high-potency bacterial vaccines using ultrashort pulsed lasers." Journal of Biophotonics, 2021.
Tsen, Shaw-Wei David, et al. "Inactivation of multidrug-resistant bacteria and bacterial spores and generation of high-potency bacterial vaccines using ultrashort pulsed lasers." Journal of Biophotonics 15.2 (2022): e202100207.
PCT/US2023/083089 filed Dec. 8, 2023, International Search Report and Written Opinion dated Jun. 3, 2024.
PCT/US2023/083767 filed Dec. 13, 2023, International Search Report and Written Opinion dated Apr. 25, 2024.
PCT/US2023/085837 filed Dec. 22, 2023, International Search Report and Written Opinion dated Apr. 9, 2024.
PCT/US2023/085839 filed Dec. 22, 2023, International Search Report and Written Opinion dated Jun. 11, 2024.
PCT/US2024/010902 filed Jan. 9, 2024, International Search Report and Written Opinion dated Apr. 24, 2024.

(56) References Cited

OTHER PUBLICATIONS

PCT/US2024/013858 filed Jan. 31, 2024, International Search Report and Written Opinion dated May 22, 2024.

\* cited by examiner

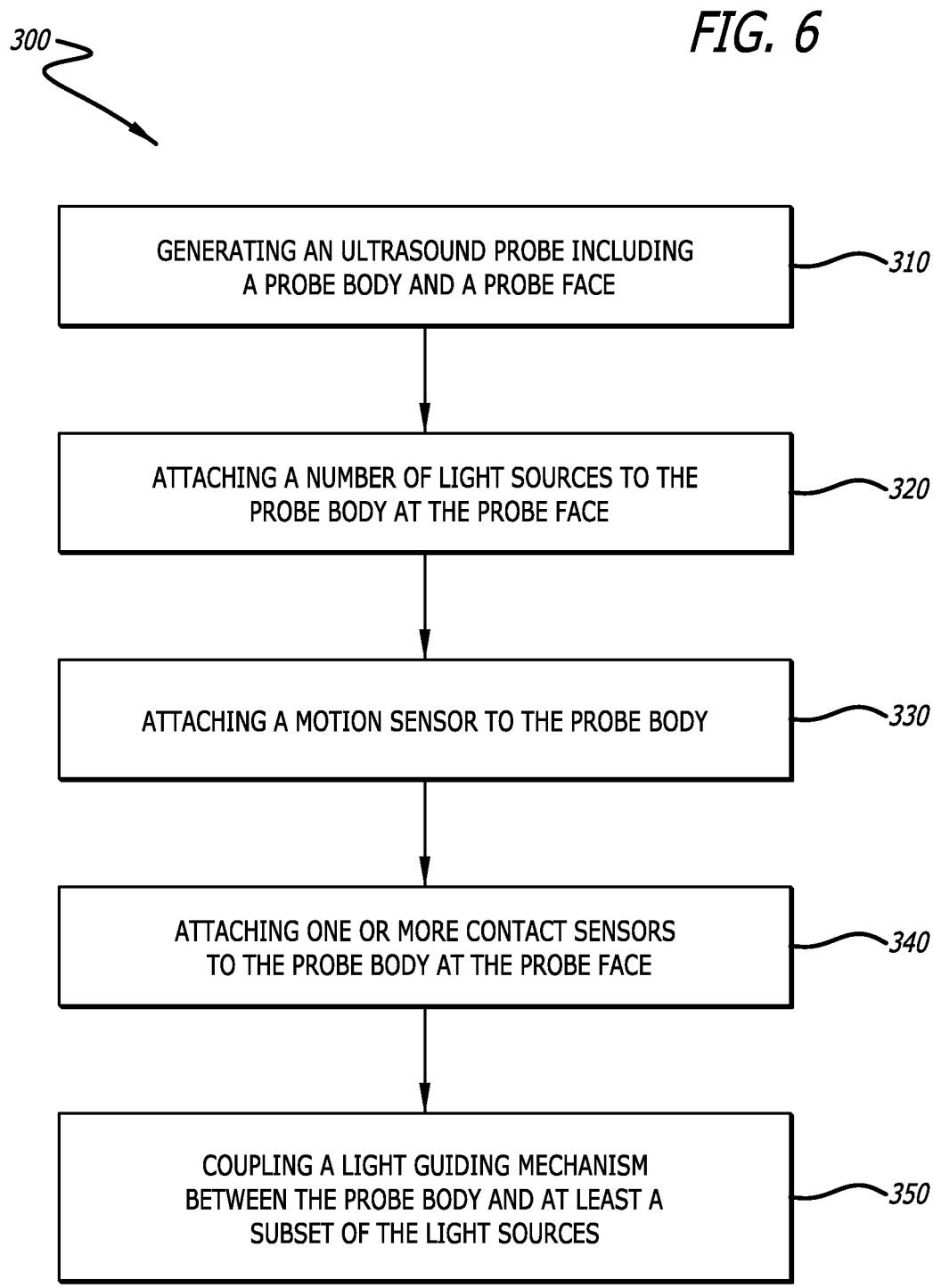

ULTRASOUND IMAGING SYSTEM WITH A STERILIZING SYSTEM

PRIORITY

This application claims the benefit of priority to U.S. Provisional Application No. 63/322,540, filed Mar. 22, 2022, which is incorporated by reference in its entirety into this application.

BACKGROUND

Placing a vascular access device can be a complicated process. Current methods utilize an ultrasound imaging system to detect and image a target vessel within the target area. Once the target vessel is located, the target area must be sterilized before the target vessel can be accessed. Then using the ultrasound imaging system to locate the target vessel, the target vessel may be accessed by a needle to place the vascular access device. It would be beneficial to the patient and to the clinician to have an ultrasound imaging system that allows the clinician to image the target vessel while sterilizing the target area, allowing the clinician to quickly access the target vessel for placing the vascular access device. Disclosed herein are an ultrasound imaging system and method of use that address the foregoing.

SUMMARY

Disclosed herein is an ultrasound imaging system that, according to some embodiments, includes comprising an ultrasound probe configured to capture an ultrasound image of a target area of a patient, where the ultrasound probe includes an array of ultrasound transducers disposed across a probe face of the ultrasound probe, and where the ultrasound transducers are in communication with a console. The ultrasound imaging system further includes a sterilizing system configured to sterilize a skin surface of the target area, where the sterilizing system has a number of light sources in communication with the console, and where the light sources are configured to project ultraviolet light away from the probe face. In some embodiments, the ultraviolet light includes a wavelength within the range of 10-400 nm.

In some embodiments, the light sources are recessed beneath an external surface of the probe face, and in some embodiments, the light sources are arranged along an outside edge of the probe face.

In some embodiments, the ultrasound probe includes one or more contact sensors coupled thereto, where the one or more contact sensors are (i) in communication with the console, and (ii) configured to detect when the probe face is in physical contact with a skin surface. In some embodiments, the one or more contact sensors includes at least one of a pressure sensor or an optical sensor.

In some embodiments, the light sources are configured to project the ultraviolet light perpendicularly away from the probe face. In some embodiments, at least a subset of the light sources are configured to be oriented between a first angular position and a second angular position with respect to the probe face. In the first angular position, the at least a subset of the light sources are configured to project the ultraviolet light at an angle of 90° in relation to the probe face, thereby sterilizing an area of the skin surface disposed directly beneath the probe face, and in the second angular position, the at least a subset of the light sources are configured to project the ultraviolet light at angle within the range of 30 degrees to 89 degrees in relation to the probe face, thereby sterilizing an area of the skin surface extending radially away from the area directly beneath the probe face.

In some embodiments, the sterilizing system is configured to sterilize the skin surface while the probe face is positioned a distance above the skin surface.

In some embodiments, the ultrasound probe includes a motion sensor in communication with the console, where the motion sensor is configured to detect movement of the ultrasound probe.

In some embodiments, the console includes at least one processor, an energy source, non-transitory computer-readable medium, and a number of logic modules. In some embodiments, the logic modules, when executed by the processor, are configured to perform operations that include activating the ultrasound transducers to capture the ultrasound image and activating the sterilizing system to sterilize the skin surface. In some embodiments, capturing an ultrasound image and activating the sterilizing system occur simultaneously.

In some embodiments, the operations further include transitioning the at least a subset of the light sources between the first angular position and the second angular position.

In some embodiments, the operations further include at least one of (i) modulating an intensity of the light sources or (ii) activating the light sources according to the defined pulsing frequency.

In some embodiments, the operations further include (i) detecting a physical contact between the probe face and skin surface via the one or more contact sensors, and (ii) activating the sterilizing system in response to detecting a physical contact between the probe face and skin surface.

In some embodiments, the operations further include (i) receiving a signal from the motion sensor and (ii) activating the sterilizing system in response to receiving the signal from the motion sensor.

In some embodiments, the operations further include (i) receiving a first signal from the motion sensor indicating that the ultrasound probe is located at a first position, (ii) recording the first position, (iii) receiving a second signal from the motion sensor subsequent the first signal indicating that the ultrasound probe is subsequently located at the first position, and (iv) at least one of deactivating the sterilizing system or providing a notification to the user in response to receiving the second signal.

Also disclosed herein is a method of capturing an ultrasound image of a target area of a patient that, according to some embodiments, includes (i) positioning an ultrasound probe over the target area; (ii) activating a sterilizing system of the ultrasound probe, where the sterilizing system has a number of light sources configured to project ultraviolet light away from a probe face of the ultrasound probe to sterilize a skin surface of the target area; (iii) placing the probe face in physical contact with the skin surface; and (iv) capturing the ultrasound image of the target area.

In some embodiments of the method, positioning an ultrasound probe over the target area includes placing the probe face in physical contact with the skin surface. In some embodiments of the method, activating the sterilizing system and capturing an ultrasound image occur simultaneously.

In some embodiments of the method, the ultrasound probe includes one or more contact sensors configured for detecting the probe face in physical contact with the skin surface, and the method further includes detecting the physical contact and activating the sterilizing system in response to detecting probe face in physical contact with the skin surface.

In some embodiments of the method, at least a subset of the light sources are configured to be oriented between a first angular position and a second angular position with respect to the probe face. In the first angular position, the at least a subset of the light sources plurality are configured to project the ultraviolet light at an angle of 90° in relation to the probe face, thereby sterilizing an area of the skin surface disposed directly beneath the probe face; and in the second angular position, the at least a subset of the light sources are configured to project the ultraviolet light at angle within the range of 30 degrees to 89 degrees in relation to the probe face, thereby sterilizing an area of the skin surface extending radially away from the area directly beneath the probe face. In such embodiments, the method further includes transitioning the at least a subset of the light sources between the first angular position and the second angular position.

In some embodiments, the method further includes modulating an intensity of the light sources.

In some embodiments of the method, the ultrasound probe includes a motion sensor in communication with the console, where the motion sensor is configured to detect movement of the ultrasound probe, and the method further includes activating the sterilizing system in response to the motion sensor detecting a predefined movement of the ultrasound probe.

In some embodiments of the method, positioning the ultrasound probe over the target area includes positioning the ultrasound probe over a first portion of the target area and at least one of (i) moving the ultrasound probe away from the first portion or (ii) deactivating the sterilizing system in response to a notification from the ultrasound probe.

Also disclosed herein is a method of manufacturing an ultrasound probe that, according to some embodiments, includes (i) generating an ultrasound probe having an array of ultrasound transducers disposed across a probe face of a probe body, where the ultrasound transducers are coupled with a console; (ii) attaching a number of light sources to the probe body at the probe face, where the light sources are configured to project ultraviolet light away from the probe face; and (iii) coupling the light sources with the console.

In some embodiments, the manufacturing method further includes attaching a motion sensor to the probe body and coupling the motion sensor with the console.

In some embodiments, the manufacturing method further includes (i) attaching one or more contact sensors to the probe body at the probe face, where the contact sensors are configured to detect a physical contact of the probe face with the skin surface, and (ii) coupling the contact sensors with the console.

In some embodiments of the manufacturing method, attaching the number of light sources includes recessing the light sources beneath an exterior surface of the probe face. In some embodiments of the manufacturing method, the light sources are configured to project the ultraviolet light perpendicularly away from the probe face, and in some embodiments of the manufacturing method, attaching the number of light sources includes arranging the light sources along an outside edge of the probe face.

In some embodiments, the manufacturing method further includes coupling a light guiding mechanism between at least a subset of the light sources and the probe body, where the at least a subset of the light sources are configured to transition between a first angular position and a second angular position with respect to the probe face. In the first angular position, the at least a subset of the light sources are configured to project the ultraviolet light at an angle of 90° in relation to the probe face, thereby sterilizing an area of the skin surface disposed directly beneath the probe face, and in the second angular position, the at least a subset of the light sources are configured to project the ultraviolet light at angle within the range of 30 degrees to 89 degrees in relation to the probe face, thereby sterilizing an area of the skin surface extending radially away from the area directly beneath the probe face.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 6 illustrates a flow chart of method of manufacturing an ultrasound probe having a sterilizing system, in accordance with some embodiments.

DESCRIPTION

Figure 1:
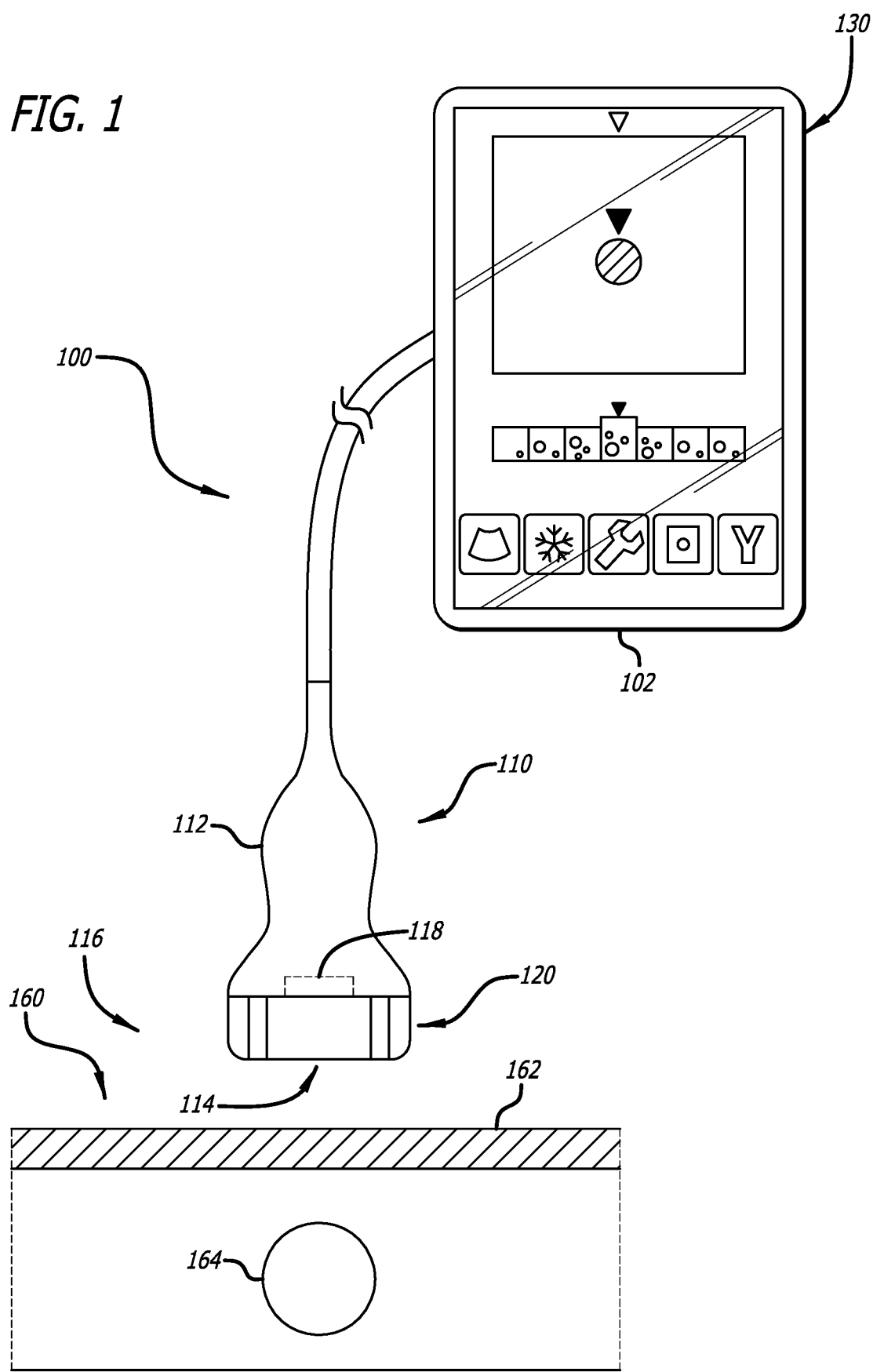
FIG. 1 illustrates a cross-sectional view of some components of an ultrasound imaging system including an ultrasound probe having a sterilizing system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, an ultrasound probe disclosed herein includes a portion of the ultrasound probe intended to be near a clinician when the ultrasound probe is used on a patient. Likewise, a "proximal length" of, for example, the ultrasound probe includes a length of the ultrasound probe intended to be near the clinician when the ultrasound probe is used on the patient. A "proximal end" of, for example, the ultrasound probe includes an end of the ultrasound probe intended to be near the clinician when the ultrasound probe is used on the patient. The proximal portion, the proximal-end portion, or the proximal length of the ultrasound probe can include the proximal end of the ultrasound probe; however, the proximal portion, the proximal-end portion, or the proximal length of the ultrasound probe need not include the proximal end of the ultrasound probe. That is, unless context suggests otherwise, the proximal portion, the proximal-end portion, or the proximal length of the ultrasound probe is not a terminal portion or terminal length of the ultrasound probe.

With respect to "distal," a "distal portion" or a "distal-end portion" of, for example, an ultrasound probe disclosed herein includes a portion of the ultrasound probe intended to be near or in a patient when the ultrasound probe is used on the patient. Likewise, a "distal length" of, for example, the ultrasound probe includes a length of the ultrasound probe intended to be near or in the patient when the ultrasound probe is used on the patient. A "distal end" of, for example, the ultrasound probe includes an end of the ultrasound probe intended to be near or in the patient when the ultrasound probe is used on the patient. The distal portion, the distal-end portion, or the distal length of the ultrasound probe can include the distal end of the ultrasound probe; however, the distal portion, the distal-end portion, or the distal length of the ultrasound probe need not include the distal end of the ultrasound probe. That is, unless context suggests otherwise, the distal portion, the distal-end portion, or the distal length of the ultrasound probe is not a terminal portion or terminal length of the ultrasound probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical, or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The phrases "connected to," "coupled to/with," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method. Additionally, all embodiments disclosed herein are combinable and/or interchangeable unless stated otherwise or such combination or interchange would be contrary to the stated operability of either embodiment.

Unless defined otherwise, all technical and scientific terms used herein have the same meaning as commonly understood by those of ordinary skill in the art.

FIG. 1 illustrates a cross-sectional view of some components of an ultrasound imaging system ("system") 100 including an ultrasound probe 110 having a sterilizing system 120 and a perspective view of a display 102 in communication with the ultrasound probe 110, in accordance with some embodiments. The sterilizing system 120 is generally configured to sterilize a skin surface 162 of a target area 160. The system 100 includes the ultrasound probe 110 having an ultrasound array 118, i.e., an array ultrasound transducers, disposed across a probe face 114 of the ultrasound probe 110, where the ultrasound array 118 is in communication with a console 130. The ultrasound array 118 is configured to capture an ultrasound image of the target area 160 which may include a target vessel 164 and/or other anatomical targets. The console 130 is coupled with the display 102. The display is configured to depict the captured ultrasound image. The probe face 114 is configured to physically contact the skin surface 162 within the target area 160.

The system 100 includes the sterilizing system 120 in communication with the console 130. The sterilizing system 120 is configured to sterilize the skin surface 162 of microbes, bacteria, and other contaminants so that a vascular access device may be safely placed within the target vessel 164. Advantageously, having the sterilizing system 120 coupled to the ultrasound probe 110 allows a user to use the ultrasound probe 110 to both capture the ultrasound image and sterilize the target area 160 before accessing the target vessel 164 with an elongate medical device (e.g., a needle or the like), thereby reducing the time needed to access the target vessel 164. The ultrasound probe 110 includes a probe body 112 and defines a distal end 116 of the ultrasound probe 110. The sterilizing system 120 may be configured to sterilize the skin surface 162 while the probe face 114 is in physical contact with the skin surface 162 or while the probe face 114 is positioned a distance above the skin surface 162.

Figure 2:
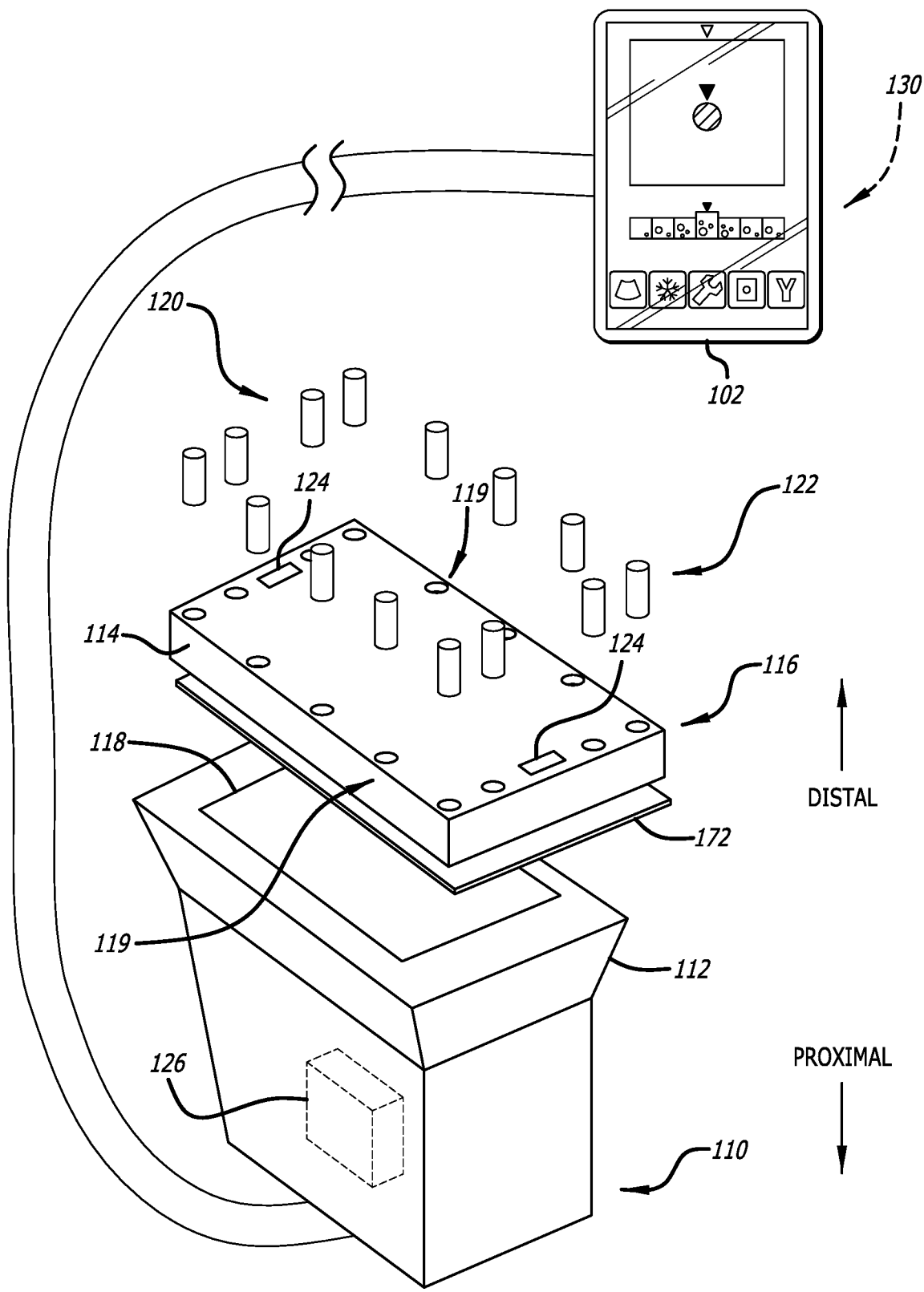
FIG. 2 illustrates an exploded perspective view of a distal portion of the ultrasound probe of FIG. 1, in accordance with some embodiments.

FIG. 2 illustrates an exploded perspective view of a distal portion of the ultrasound probe 110 including the sterilizing system 120, in accordance with some embodiments. The ultrasound array 118 is configured to capture the ultrasound images while the probe face 114 is in physical contact the skin surface 162.

In some embodiments, the ultrasound probe 110 may include a motion sensor 126, such as a gyroscope, an accelerometer, or an inertia measurement unit (IMU), for example, where the motion sensor 126 is in communication with the console 130, and where the motion sensor 126 is configured to detect movement/motion of the ultrasound probe 110 in three-dimensional space. In some embodiments, the motion sensor 126 may enable recording and/or tracking of a position of the ultrasound probe 110.

In some embodiments, the ultrasound probe may include one or more contact sensors 124 coupled with the ultrasound probe 110 at the probe face 114, where one or more contact sensors 124 are in communication with the console 130. In some embodiments, the one or more contact sensors 124 may be configured to detect a physical contact of the probe face 114 with the skin surface 162. In some embodiments, the one or more contact sensors 124 may include optical sensors, pressure sensors, or the like.

The sterilizing system 120 includes a number of light sources 122 configured to project an ultraviolet (UV) light. The light sources 122 may be coupled to the probe face 114. In some embodiments, the light sources 122 may be arranged along an outside edge 119 of the probe face 114. In some embodiments, the light sources 122 may be arranged in a variety of different arrangements including along the outside edge 119 or anywhere on the probe face 114. In some embodiments, the light sources 122 may be in communication with the console 130 and may be activated by the console 130 to sterilize the skin surface 162. In some embodiments, the light sources 122 may be coupled to the probe face 114 or may be embedded into the probe face 114, so that the light sources 122 may be flush against the probe face 114 or beneath an exterior surface of the probe face 114. In some embodiments, each of the light sources 122 may be arranged in a vertical orientation, i.e., so that light is projected away perpendicularly away from the probe face 114. In some embodiments, a first subset of the light sources 122 may be configured to be angled radially inward toward a center of the probe face 114 and/or a second subset of the light sources 122 may be angled radially outward away from the probe face 114. In an embodiment, the ultrasound probe 110 may include a motorized light guiding mechanism 172 operatively coupled with a third subset of the light sources 122, where the light guiding mechanism 172 is configured to orient each of the third subset of the light sources 122 anywhere between a first angular position wherein the third subset of the light sources 122 are angled perpendicular to the probe face 114 or inward towards the center of the probe face 114 and a second angular position wherein the third subset of the light sources 122 are angled outward away from the probe face 114 so as to project onto a portion of the skin surface disposed radially outward of the probe face 114. Advantageously, having the third subset of the light sources 122 configured to move between the first angular position and the second angular position may allow a greater surface area of the target area 160 to be sterilized by the light sources 122.

In some embodiments, the light sources 122 may be configured to generate a UV light within the UV spectrum (e.g., include a wavelength within the range of 10-400 nm). In some embodiments, the light sources 122 may be configured to generate the UV light within the UV spectrum and a light within the visible spectrum (e.g., 380-700 nm). In some embodiments, the light sources 122 may be configured to generate one or more specific wavelengths within the UV spectrum including within the range of UVA (315-400 nm), UVB (280-315 nm), and/or UVC (100-280 nm). In some embodiments, the light sources 122 may be activated for a defined duration of time, pulsed at a defined frequency or the like, to sterilize the skin surface 162. In some embodiments, the light sources 122 may be configured to generate a defined intensity of the UV light as will be described in more detail herein. In some embodiments, the light sources 122 may be configured to be activated individually, in groups, and/or all at the same time.

Figure 3:
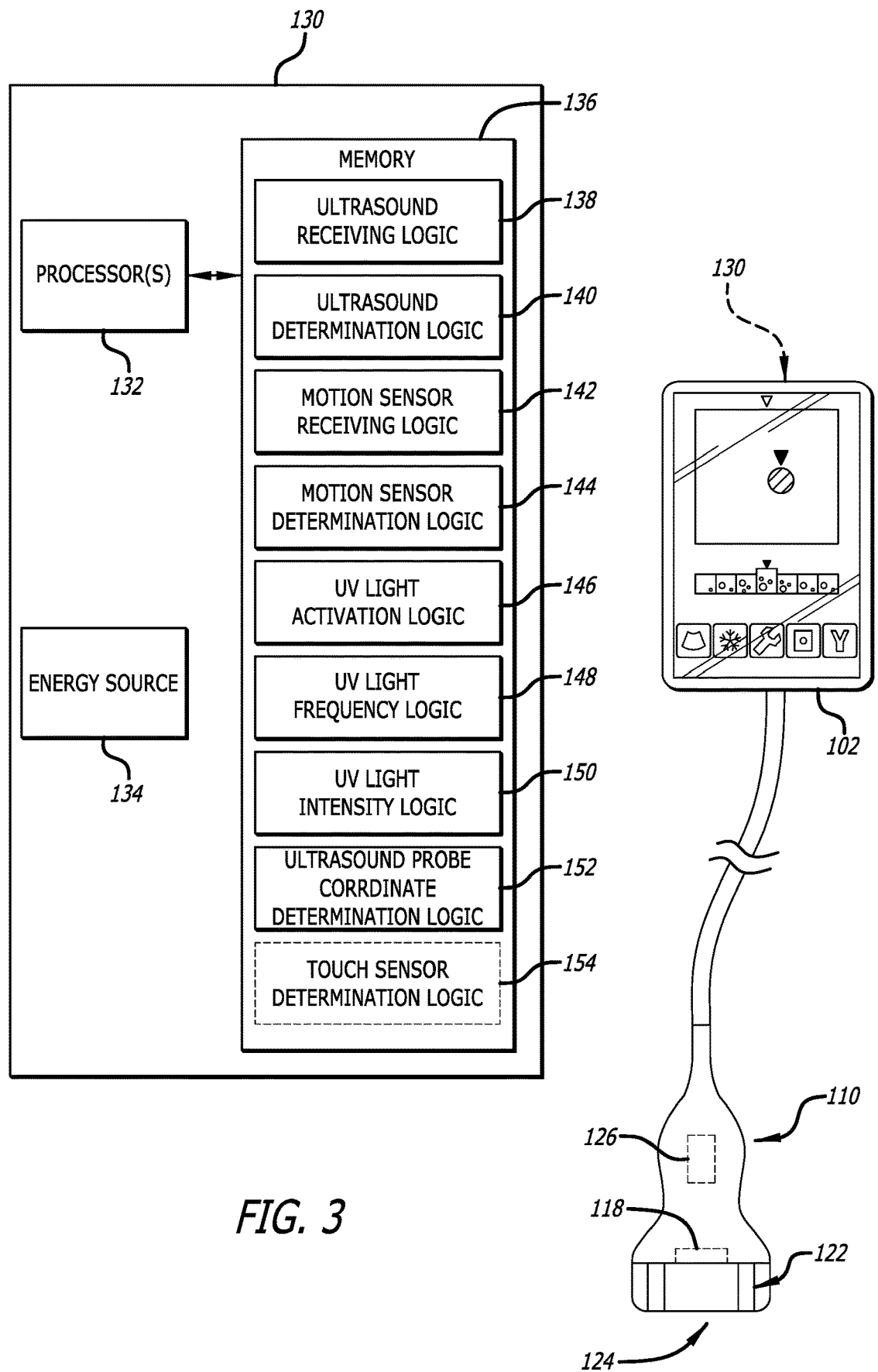
FIG. 3 illustrates a block diagram of some components of the ultrasound imaging system of FIG. 1 including a console, in accordance with some embodiments.

FIG. 3 illustrates a block diagram of some components of the system 100 including the console 130, in accordance with some embodiments. In some embodiments, the console 130 may be in communication with each of the ultrasound array 118, the light sources 122, the one or more contact sensors 124, the motion sensor 126, and the display 102. In some embodiments, the display 102 may include a touch screen display configured to allow a user to adjust various parameters of the sterilizing system 120. In some embodiments, the console 130 may be configured to activate and manipulate various features of the light sources 122 to effectively sterilize the skin surface 162. For example, the console 130 may be configured to adjust the intensity of the light sources 122, the duration of the UV light activation, a pulsing frequency of the light sources 122, or a combination thereof. In some embodiments, the console 130 includes a number (e.g., 1, 2, 3, or more) of processors 132, an energy source 134, non-transitory computer readable medium ("memory") 136, and a number (e.g., 1, 2, 3, or more) of logic modules.

In some embodiments, the logic modules may include an ultrasound receiving logic 138, an ultrasound determination logic 140, a motion sensor receiving logic 142, a motion sensor determination logic 144, an UV light activation logic 146, an UV light frequency logic 148, an UV light intensity logic 150, an ultrasound probe coordinate determination logic 152, or a touch sensor determination logic 154. In some embodiments, the ultrasound receiving logic 138 may be configured to receive the ultrasound image captured by the ultrasound array 118. In some embodiments, the ultrasound determination logic 140 may be configured to automatically determine the target vessel 164 within the ultrasound image captured by the ultrasound array 118.

In some embodiments, the motion sensor receiving logic 142 may be configured to receive motion sensor values from the motion sensor 126. In some embodiments, the motion sensor determination logic 144 may be configured to determine movement of the ultrasound probe 110. In some embodiments, the motion sensor determination logic 144 may be configured to determine if the motion sensor values are above an established movement threshold, wherein motion sensor values above the established movement threshold indicate the ultrasound probe 110 is currently in motion and motion sensor values below the established movement threshold indicate the ultrasound probe 110 is not currently in motion. In some embodiments, the motion sensor determination logic 144 may detect a defined movement, such as predetermined movement (e.g., a jiggle) stored in the memory 136.

In some embodiments, the motion sensor receiving logic 142 may be configured to receive a first signal from the motion sensor 126 indicating that the ultrasound probe 110 is located at a first position. The motion sensor receiving logic 142 may also be configured to record the first position. The motion sensor receiving logic 142 may further be configured to receive a second signal from the motion sensor 126 subsequent to the first signal indicating that the ultrasound probe 110 is again or still located at the first position. In some embodiments, the motion sensor determination logic 144 may be configured to track the location of the ultrasound probe 110 such as between the first position and a second position. As such, the motion sensor determination logic 144 may be configured to track area portions of the target area 160 that have been sterilized, i.e., exposed to UV light.

In some embodiments, the UV light activation logic 146 may be configured to activate or deactivate the light sources 122. In some embodiments, the UV light activation logic 146 may be configured to activate the light sources 122 in response to user input including user input on the display 102 or user input on the ultrasound probe 110 (e.g., a button press or the like). In some embodiments, the UV light activation logic 146 may be configured to automatically activate the light sources 122 in response to movement or lack of movement of the ultrasound probe 110. In some embodiments, the UV light activation logic 146 may be configured to automatically activate the light sources 122 if the motion sensor values are below an established movement threshold. In some embodiments, the UV light activation logic 146 may be configured to activate the sources 122 in response to an ultrasound probe gesture (e.g., a defined movement set, motion, or movement pattern of the ultrasound probe 110). In some embodiments, the UV light activation logic 146 may be configured to activate each of the light sources 122 individually, as groups, as an entirety of the light sources 122.

As discussed above, the third subset of the light sources 122 may be configured to transition between the first angular position, wherein the third subset of light sources 122 are perpendicular to the probe face 114, i.e., project the UV light at an angle of 90 degrees with respect to the probe face 114 so as to sterilize an area of the skin surface 162 directly underneath the probe face 114. In some embodiments, in the second angular position, the third subset of light sources 122 may be angled radially outward at any angle within the range of 30-89° in relation to the probe face 114 to sterilize an area of the skin surface 162 disposed radially outward of the probe face 114.

In an embodiment, the light sources 122 or a subset thereof may be moveable toward and away from the exterior surface of the probe face 114 so that the light sources 122 are moveable toward and away from the skin surface 162 between a first vertical position and a second vertical position, where the first vertical position is closer to the skin surface 162 that the second vertical position. In some embodiments, the UV light activation logic 146 may be configured to move the light sources 122 (i) toward the first vertical position to increase the UV light intensity at the skin surface 162 or (ii) toward the second vertical position to decrease the UV light intensity at the skin surface 162. In some embodiments, the UV light activation logic 146 may be configured to transition a subset of light sources 122 anywhere between the first and second angular positions and the first and second vertical positions. In some embodiments, the UV light activation logic 146 may be configured to move the light sources 122 in response to movement of the ultrasound probe 110, lack of movement of the ultrasound probe 110, or physical contact of the ultrasound probe 110 with the skin surface 162.

In some embodiments, the UV light activation logic 146 may be configured to generate an illumination program that controls one or more parameters of the light sources 122 including activating the light sources 122 at a defined pulsing frequency and/or a defined intensity for a specific duration of time to sterilize the skin surface 162 within the target area 160. In some embodiments, the illumination program may be informed by known UV light frequencies, known UV light intensities, and known durations of time needed to sterilize the skin surface 162 from microbes, bacteria, or other contaminants.

In some embodiments, the UV light frequency logic 148 may be configured to adjust the pulsing frequency of light sources 122 in response to user input, movement of the ultrasound probe 110, or physical contact of the ultrasound probe 110 with the skin surface. In some embodiments, the UV light intensity logic 150 may be configured to adjust the intensity of the light sources 122. In some embodiments, the UV light intensity logic 150 may be configured to adjust the intensity of the light sources 122 in response to user input, movement of the ultrasound probe 110, lack of movement of the ultrasound probe 110, or physical contact of the ultrasound probe 110 with the skin surface 162. In some embodiments, wherein the ultrasound probe 110 includes the one or more contact sensors 124, the touch sensor determination logic 154 may be configured to determine if the ultrasound probe 110 is in physical contact with the skin surface 162. In some embodiments, the sterilizing system 120 may be activated only when the probe face 114 is in physical contact with the skin surface 162. In an embodiment, the ultrasound array 118 may be configured to capture ultrasound images only when the probe face 114 is in physical contact with the skin surface 162. In some embodiments, the UV light activation logic 146 may activate the light sources 122 in response to detecting that the probe face 114 is in physical contact with the skin surface 162.

In some embodiments, the ultrasound probe coordinate determination logic 152 may be configured to determine the coordinates (i.e., position) of the ultrasound probe 110 within the target area 160. In some embodiments, the ultrasound probe coordinate determination logic 152 may be configured to use motion sensor values received from the motion sensor 126 to determine the location (e.g., coordinates) of the ultrasound probe 110 within the target area 160. In some embodiments, the ultrasound probe coordinate determination logic 152 may be configured to track and record the location of the ultrasound probe 110 within the target area 160. Accordingly, the UV light activation logic 146 may use the recorded tracking information to determine which area portions within the target area 160 have yet to be sterilized and which area portions within the target area 160 have been sterilized. In some embodiments, the ultrasound probe coordinate determination logic 152 may be configured to provide notification to the user when the ultrasound probe 110 is subsequently located a previous position when the sterilization system 120 is activated.

In some embodiments, the ultrasound probe determination logic 152 may be configured to generate feedback (i.e., provide notification) to the user indicating that area portions of the target area 160 have not yet been sterilized. In some embodiments, the ultrasound probe determination logic 152 may be configured to direct the user to area portions (i.e., coordinates) within the target area 160 that need to be sterilized via visual feedback on the display 102, auditory direction from the console 130, haptic feedback through the ultrasound probe 110, or the like. In some embodiments, the ultrasound probe coordinate determination logic 152 may be configured to use information or data from other tracking mechanisms (not shown), such as fiber optic systems, for example, to determine the location or coordinates of the ultrasound probe 110 within the target area 160 in order to activate the sterilization system 120 to sterilize the target area 160.

In some embodiments, the UV light activation logic 146 may activate the light sources 122 only when the ultrasound probe 110 is located at new coordinates within the target area 160. Similarly, the UV light activation logic 146 may deactivate the light sources 122 when the ultrasound probe 110 is located at previous coordinates within the target area 160. Advantageously, by only activating the light sources 122 when the ultrasound probe 110 is located at new coordinates within the target area 160, the sterilizing system 120 may avoid excessive exposure of the light sources 122 to the skin surface 162 and may ensure that the skin surface 162 receives only the UV light sufficient for sterilization.

Figure 4A:
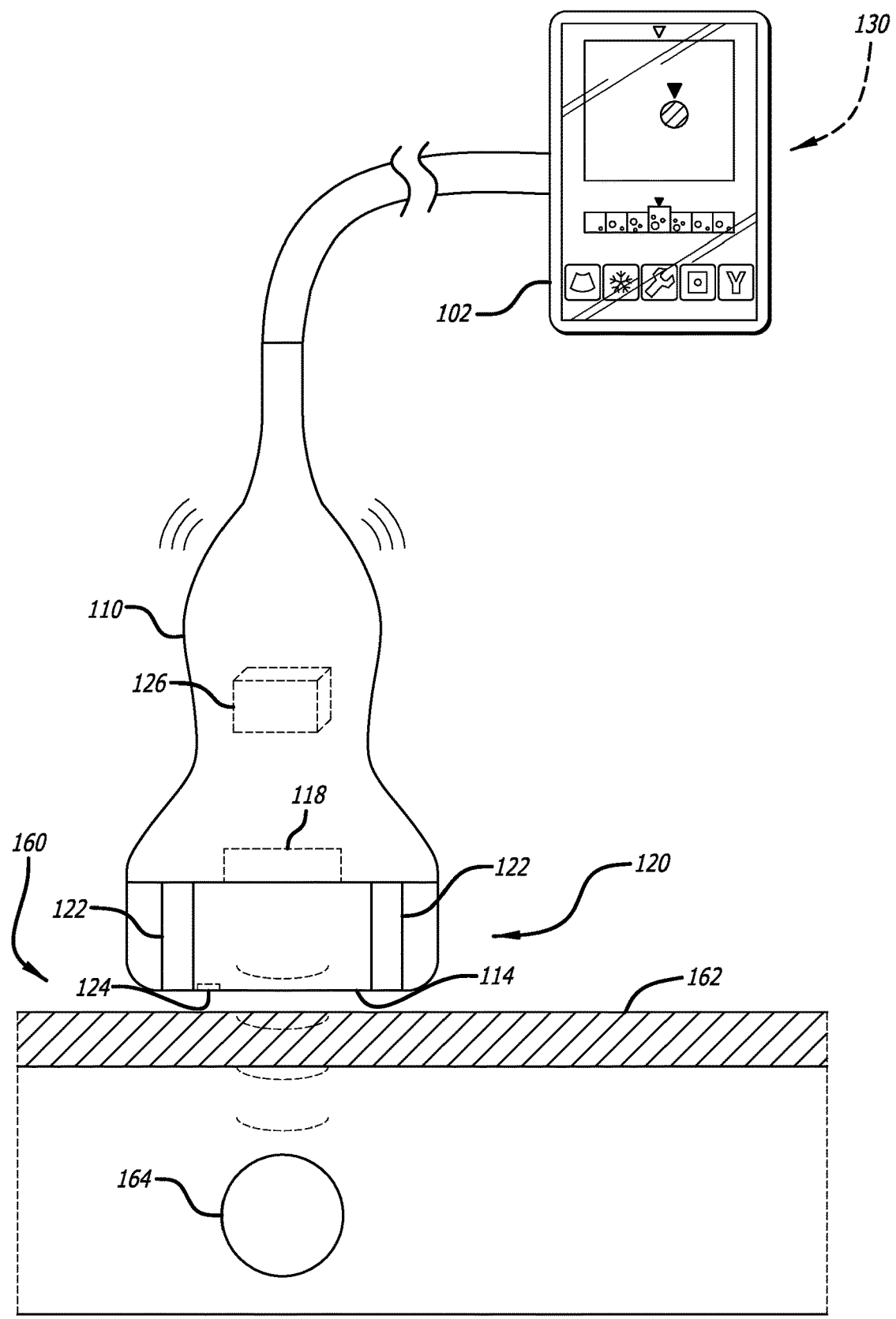
FIGS. 4A-4C illustrate a cross-sectional views of the system of FIG. 1 depicting an exemplary method of imaging a target are and sterilizing a skin surface of the target area, in accordance with some embodiments.
Figure 4B:
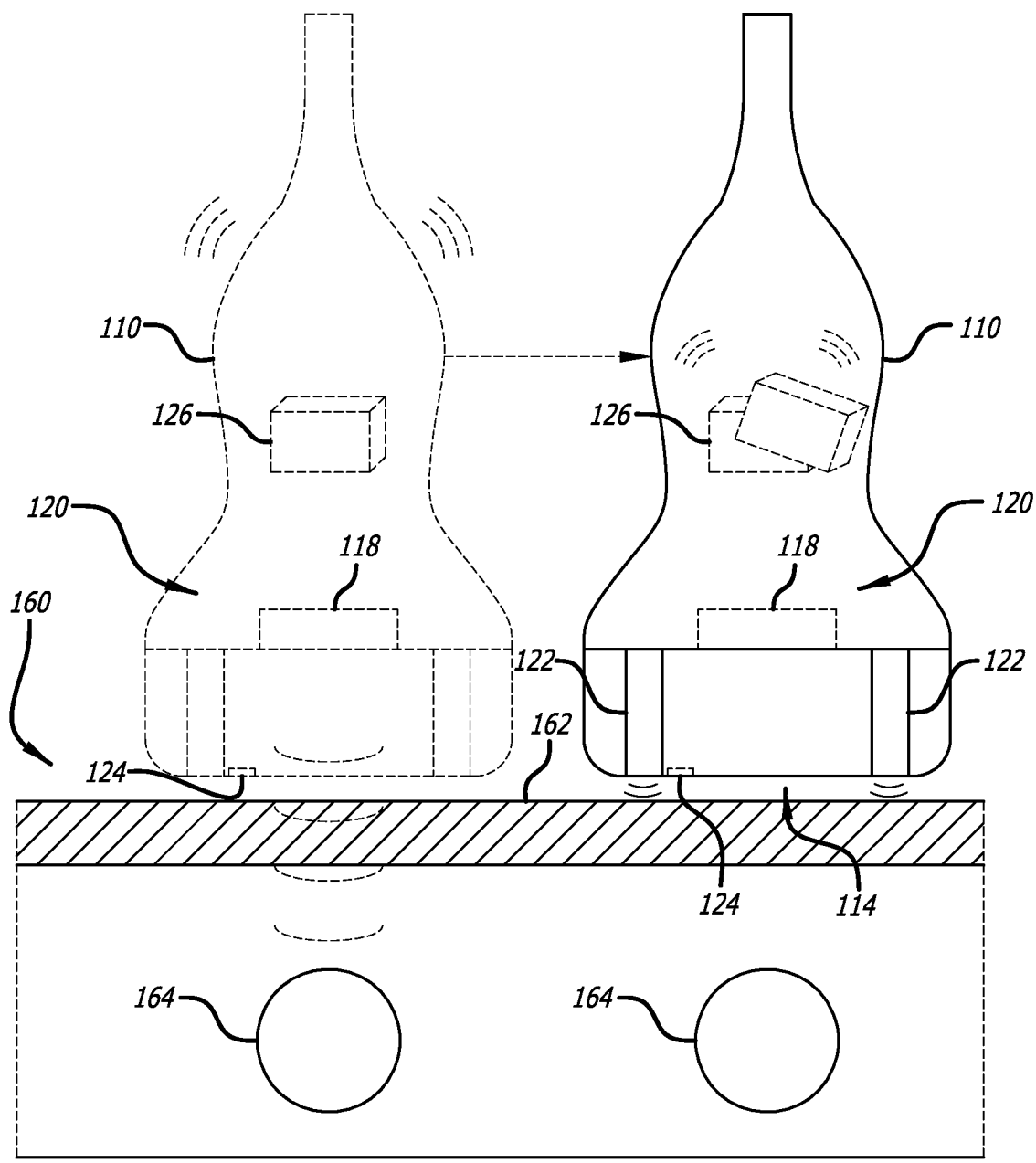
Figure 4C:
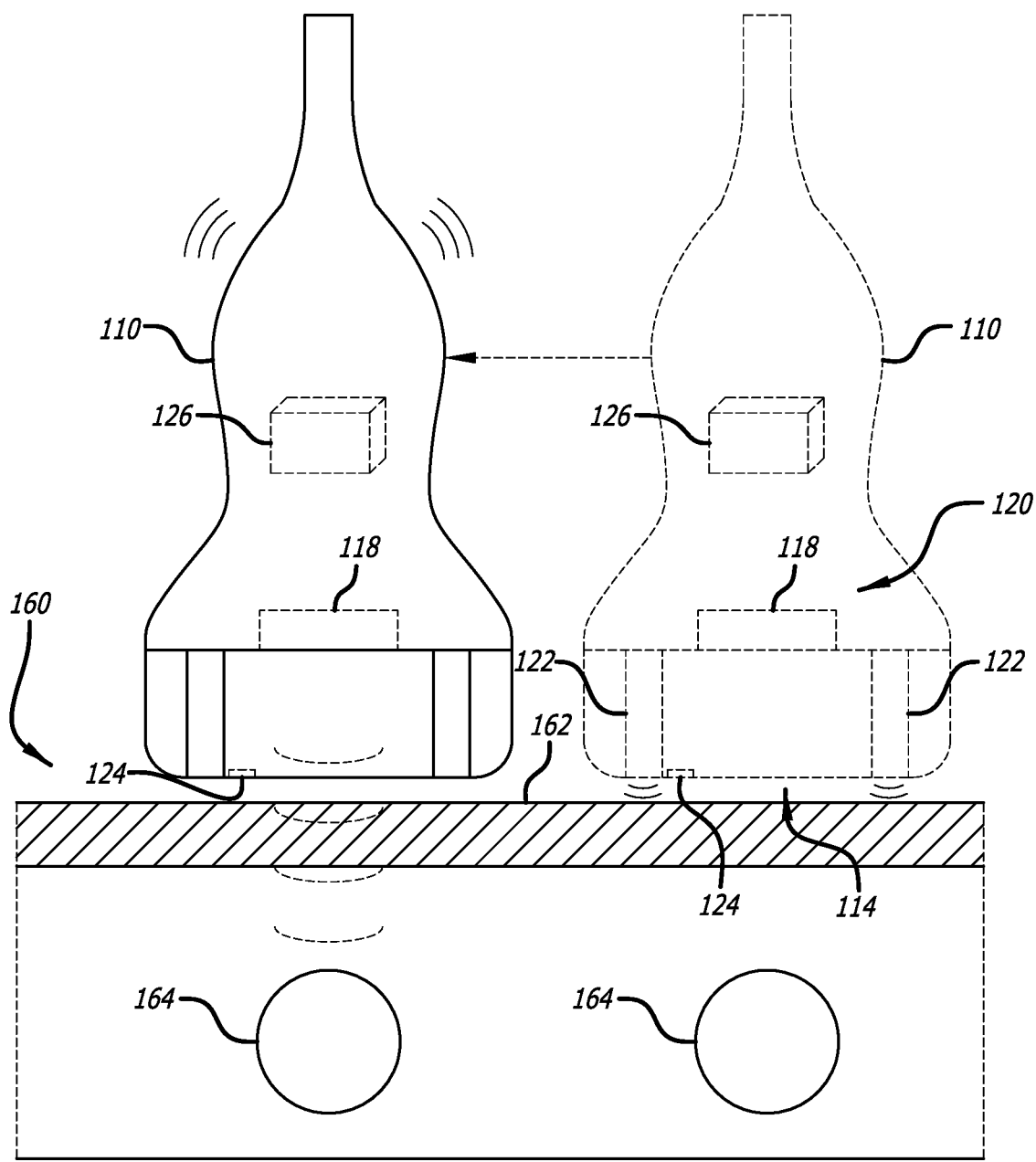

FIGS. 4A-4C illustrate the system 100 during the performance of an exemplary method of imaging a target area 160 and sterilizing the skin surface 162 within the target area 160 using the sterilizing system 120, in accordance with some embodiments. As illustrated in FIG. 4A, the ultrasound probe 110 may be brought into the target area 160 to capture an ultrasound image of a target vessel 164. In some embodiments, the one or more contact sensors 124 may be configured to detect the ultrasound probe 110, including the probe face 114, being in physical contact with the skin surface 162. In some embodiments, the ultrasound array 118 and the sterilizing system 120 may be used simultaneously or the ultrasound array 118 may be used independent of the sterilizing system 120. The console 130 may be configured to receive the ultrasound image from the ultrasound array 118 and display the ultrasound image on the display 102.

As illustrated in FIG. 4B, once movement of the ultrasound probe 110 has stopped, as detected by the motion sensor 126 and the console 130, the sterilizing system 120 may be actuated to sterilize the skin surface 162 below the probe face 114. In some embodiments, the light sources 122 may be activated for a specific time to sterilize the skin surface 162 below the probe face 114. It can be appreciated that the space between the probe face 114 and the skin surface 162 in FIGS. 4A-4C may exist while the light sources 122 illuminate the skin surface 162 to sterilize the skin surface 162.

Once the skin surface 162 below the probe face 114 has been sterilized, the console 130 may provide feedback to the user (e.g., haptic feedback from the ultrasound probe 110, audio feedback from the console 130, a visual message on the display 102, or the like) indicating that the skin surface 162 underneath the probe face 114 has been sterilized. The console 130 may be configured to direct the user through feedback (e.g., haptic feedback from the ultrasound probe 110, audio feedback from the console 130, a visual message on the display 102, or the like) to move the ultrasound probe 110 to other location coordinates within the target area 160 to sterilize a different area of the skin surface 162. In some embodiments, the console 130 may be configured to detect when the skin surface 162 receives sufficient UV light to sterilize the skin surface 162 and may be configured to provide feedback to the user in order to ensure the skin surface 162 below the probe face 114 is not damaged or injured by the UV light from the light sources 122.

As illustrated in FIG. 4C, if the ultrasound probe 110 has movement above a movement threshold as detected by the motion sensor 126 or the one or more contact sensors 124 detect an absence of physical contact with the skin surface 162, the sterilizing system 120 may be configured to automatically deactivate the light sources 122 from generating the UV light, thereby reducing the likelihood of UV light exposure to other areas of the patient including the eyes, the head, the neck, or the like. In some embodiments, the console 130 may be configured to generate feedback to the user (e.g., a visual message on the display 102, haptic feedback from the ultrasound probe 110, audio feedback from the console 130, or the like) indicating the sterilizing system 120 is not actively sterilizing the skin surface 162.

Figure 5:
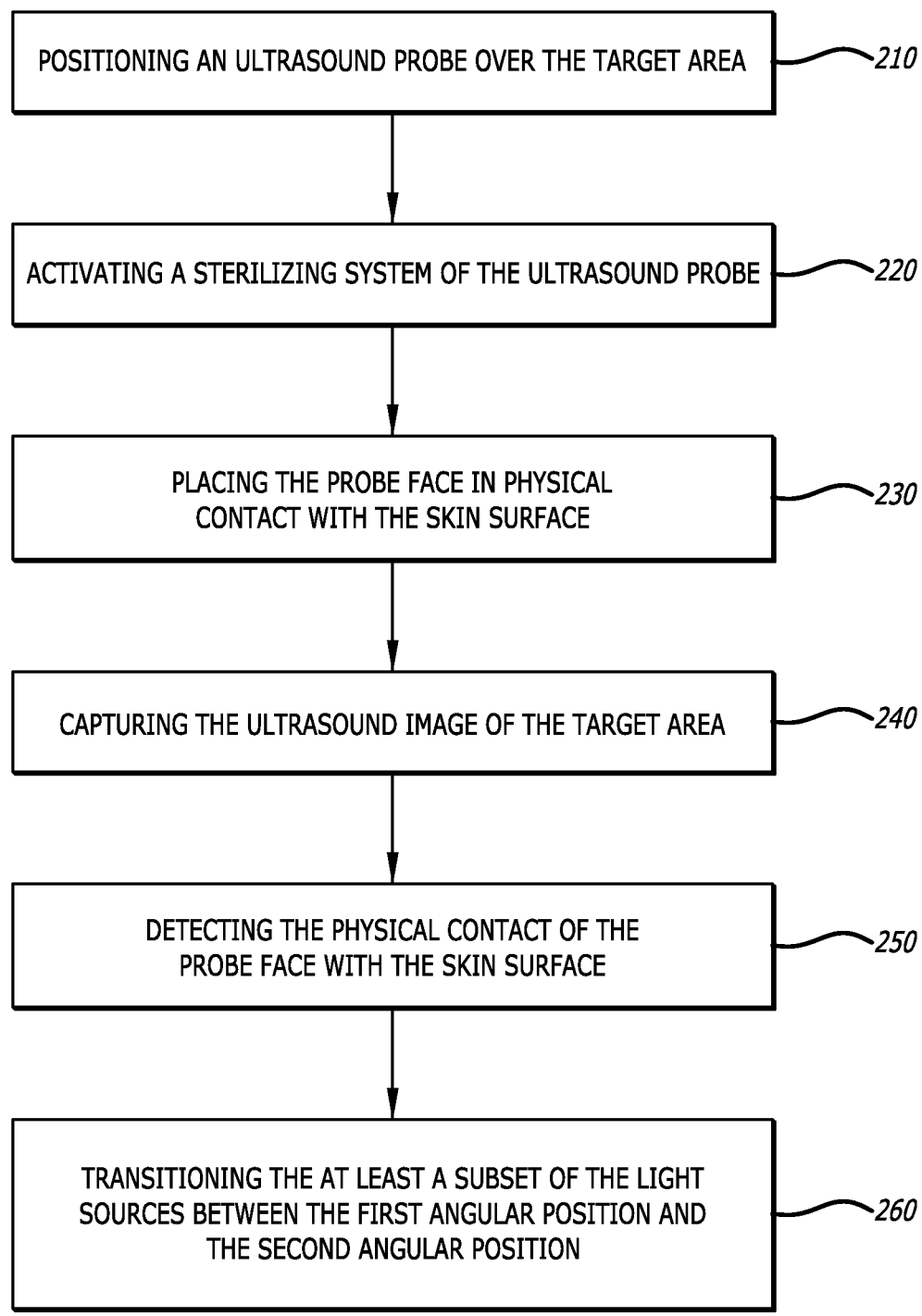
FIG. 5 illustrates a flow chart of an exemplary method of capturing an ultrasound image, in accordance with some embodiments.

FIG. 5 illustrates a flow chart of an exemplary method 200 of capturing an ultrasound image of a target area of a patient that, according to some embodiments. The method 200 includes positioning an ultrasound probe over the target area (block 210). In some embodiments of the method 200, positioning the ultrasound probe over the target area includes positioning the ultrasound probe over a first portion of the target area and at least one of (i) moving the ultrasound probe away from the first portion or (ii) deactivating the sterilizing system in response to a notification from the ultrasound probe.

The method 200 may further include activating a sterilizing system of the ultrasound probe (block 220), where the sterilizing system has a number of light sources configured to project ultraviolet light away from a probe face of the ultrasound probe to sterilize a skin surface of the target area. In some embodiments of the method 200 positioning an ultrasound probe over the target area includes placing the probe face in physical contact with the skin surface. In some embodiments, the method 200 may further include modulating an intensity of the light sources. In some embodiments of the method 200, the ultrasound probe includes a motion sensor in communication with the console, where the motion sensor is configured to detect movement of the ultrasound probe, and in such embodiments, the method 200 may further include activating the sterilizing system in response to the motion sensor detecting a predefined movement of the ultrasound probe.

The method 200 may further include placing the probe face in physical contact with the skin surface (block 230) so that the ultrasound probe may sonically couple with the skin surface, thereby facilitating ultrasound transmission into and out of the target area. The method 200 may further include capturing the ultrasound image of the target area (block 240). In some embodiments of the method 200, activating the sterilizing system and capturing an ultrasound image occur simultaneously.

In some embodiments of the method 200, the ultrasound probe may include one or more contact sensors configured to detect the physical contact with the skin surface, and in such embodiments, the method 200 may further include detecting the physical contact of the probe face with the skin surface (block 250) and in such embodiments, the method 200 may further include activating the sterilizing system in response to detecting the physical contact with the skin surface.

In some embodiments of the method 200, at least a subset of the light sources are configured to be oriented between a first angular position and a second angular position with respect to the probe face. In the first angular position, the at least a subset of the light sources plurality are configured to project the ultraviolet light at an angle of 90° in relation to the probe face, thereby sterilizing an area of the skin surface disposed directly beneath the probe face; and in the second angular position, the at least a subset of the light sources are configured to project the ultraviolet light at angle within the range of 30 degrees to 89 degrees in relation to the probe face, thereby sterilizing an area of the skin surface extending radially away from the area directly beneath the probe face. In such embodiments, the method 200 may further include transitioning the at least a subset of the light sources between the first angular position and the second angular position (block 260)

FIG. 6 illustrates a flow chart of an exemplary method 300 of manufacturing an ultrasound probe, according to some embodiments, The method 300 may include generating an ultrasound probe (block 310) including a probe body and a probe face, where the ultrasound probe includes an array of ultrasound transducers disposed across a probe face of a probe body, and where the ultrasound transducers are coupled with a console of an ultrasound imaging system.

The method 300 may further include attaching a number of light sources to the probe body at the probe face (block 320), where the light sources are configured to project ultraviolet light onto and sterilize a skin surface. In some embodiments of the method 300, attaching the light sources light sources to the probe body includes coupling the light sources with the console. In some embodiments of the method 300, attaching the number of light sources includes recessing the light sources beneath an exterior surface of the probe face. In some embodiments of the method 300, the light sources are configured to project the ultraviolet light perpendicularly away from the probe face, and in some embodiments of the method 300, attaching the number of light sources includes arranging the light sources along an outside edge of the probe face.

In some embodiments, the method 300 further includes attaching a motion sensor to the probe body (block 330). In such embodiments, attaching a motion sensor to the probe body includes coupling the motion sensor with the console.

In some embodiments, the method 300 may further include attaching one or more contact sensors to the probe body at the probe face (block 340), where the contact sensors are configured to detect a physical contact of the probe face with the skin surface. In such embodiments, attaching one or more contact sensors to the probe body includes coupling the contact sensors with the console.

In some embodiments, the method 300 includes coupling a light guiding mechanism between the probe body and at least a subset of the light sources (block 350), where the at least a subset of the light sources are configured to transition between a first angular position and a second angular position with respect to the probe face. In the first angular position, the at least a subset of the light sources are configured to project the ultraviolet light at an angle of 90° in relation to the probe face, thereby sterilizing an area of the skin surface disposed directly beneath the probe face, and in the second angular position, the at least a subset of the light sources are configured to project the ultraviolet light at angle within the range of 30 degrees to 89 degrees in relation to the probe face, thereby sterilizing an area of the skin surface extending radially away from the area directly beneath the probe face.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound imaging system, comprising:
    an ultrasound probe configured to capture an ultrasound image of a target area of a patient, wherein:
        the ultrasound probe includes an array of ultrasound transducers disposed across a probe face of the ultrasound probe, and
        the ultrasound transducers are in communication with a console; and
    a sterilizing system configured to sterilize a skin surface of the target area, wherein:
        the sterilizing system includes a number of light sources in communication with the console, and
        the number of light sources are configured to project ultraviolet light away from the probe face.

2. The system according to claim 1, wherein the ultraviolet light includes a wavelength within a range of 10-400 nm.

3. The system according to claim 1, wherein the number of light sources are recessed beneath an external surface of the probe face.

4. The system according to claim 1, wherein the number of light sources are arranged along an outside edge of the probe face.

5. The system according to claim 1, wherein the number of light sources are configured to project the ultraviolet light perpendicularly away from the probe face.

6. The system according to claim 1, wherein the sterilizing system is configured to sterilize the skin surface while the probe face is positioned a distance above the skin surface.

7. The system according to claim 1, wherein the console includes at least one processor, an energy source, a non-transitory computer-readable medium, and a number of logic modules.

8. The system according to claim 7, wherein the number of logic modules, when executed by the at least one processor, are configured to perform operations including:
    activating the ultrasound transducers to capture the ultrasound image; and
    activating the sterilizing system to sterilize the skin surface.

9. The system according to claim 7, wherein capturing the ultrasound image and activating the sterilizing system occur simultaneously.

10. The system according to claim 7, wherein:
    at least a subset of the number of light sources are configured to be oriented between a first angular position and a second angular position with respect to the probe face;
    in the first angular position, the at least the subset of the number of light sources are configured to project the ultraviolet light at an angle of 90° in relation to the probe face, thereby sterilizing an area of the skin surface disposed directly beneath the probe face; and
    in the second angular position, the at least the subset of the number of light sources are configured to project the ultraviolet light at an angle within a range of 30 degrees to 89 degrees in relation to the probe face, thereby sterilizing the area of the skin surface extending radially away from the area directly beneath the probe face.

11. The system according to claim 10, wherein the system further includes transitioning the at least the subset of the number of light sources between the first angular position and the second angular position.

12. The system according to claim 7, wherein the systems further includes at least one of modulating an intensity of the number of light sources or activating the number of light sources according to a defined pulsing frequency.

13. The system according to claim 7, wherein:
the ultrasound probe includes one or more contact sensors coupled thereto, and
the one or more contact sensors are:
in communication with the console, and
configured to detect when the probe face is in physical contact with the skin surface.

14. The system according to claim 13, wherein the one or more contact sensors include at least one of a pressure sensor or an optical sensor.

15. The system according to claim 13, wherein the system further includes:
detecting the physical contact between the probe face and the skin surface via the one or more contact sensors; and
activating the sterilizing system in response to detecting the physical contact between the probe face and the skin surface.

16. The system according to claim 7, wherein the ultrasound probe includes a motion sensor in communication with the console, the motion sensor configured to detect movement of the ultrasound probe.

17. The system according to claim 16, wherein the system further includes:
receiving a signal from the motion sensor; and
activating the sterilizing system in response to receiving the signal from the motion sensor.

18. The system according to claim 16, wherein the system further includes:
receiving a first signal from the motion sensor indicating that the ultrasound probe is located at a first position;
recording the first position;
receiving a second signal from the motion sensor subsequent the first signal indicating that the ultrasound probe is located at the first position; and
in response to receiving the second signal, at least one of (i) deactivating the sterilizing system or (ii) providing a notification.

19. A method of capturing an ultrasound image of a target area of a patient, comprising:
positioning an ultrasound probe over the target area;
activating a sterilizing system of the ultrasound probe, the sterilizing system having a number of light sources configured to project ultraviolet light away from a probe face of the ultrasound probe to sterilize a skin surface of the target area;
placing the probe face in physical contact with the skin surface; and
capturing the ultrasound image of the target area.

20. The method according to claim 19, wherein positioning the ultrasound probe over the target area includes placing the probe face in physical contact with the skin surface.

21. The method according to claim 19, wherein the ultrasound probe includes one or more contact sensors configured for detecting the probe face in physical contact with the skin surface, the method further comprising:
detecting the physical contact with the skin surface, and
activating the sterilizing system in response to detecting the physical contact with the skin surface.

22. The method according to claim 19, wherein activating the sterilizing system and capturing the ultrasound image occur simultaneously.

23. The method according to claim 19, wherein:
at least a subset of the number of light sources are configured to be oriented between a first angular position and a second angular position with respect to the probe face;
in the first angular position, a plurality of the at least the subset of the light sources are configured to project the ultraviolet light at an angle of 90° in relation to the probe face, thereby sterilizing an area of the skin surface disposed directly beneath the probe face;
in the second angular position, the at least the subset of the number of light sources are configured to project the ultraviolet light at an angle within the range of 30 degrees to 89 degrees in relation to the probe face, thereby sterilizing the area of the skin surface extending radially away from the area directly beneath the probe face; and
the method further comprises transitioning the at least the subset of the number of light sources between the first angular position and the second angular position.

24. The method according to claim 19, further comprising modulating an intensity of the number of light sources.

25. The method according to claim 19, wherein:
the ultrasound probe includes a motion sensor in communication with a console, the motion sensor configured to detect movement of the ultrasound probe, and
the method further comprises activating the sterilizing system in response to the motion sensor detecting a predefined movement of the ultrasound probe.

26. The method according to claim 19, wherein positioning the ultrasound probe over the target area includes:
positioning the ultrasound probe over a first portion of the target area, and
in response to a notification from the ultrasound probe, at least one of (i) moving the ultrasound probe away from the first portion or (ii) deactivating the sterilizing system.

* * * * *